(12) United States Patent
Mitsuhashi

(10) Patent No.: US 7,258,976 B2
(45) Date of Patent: Aug. 21, 2007

(54) METHOD OF PREPARING CELL LYSATE

(75) Inventor: Masato Mitsuhashi, Irvine, CA (US)

(73) Assignees: Hitachi Chemical Co. Ltd., Tokyo (JP); Hitachi Chemical Research Center, Inc., Irvine, CA (US)

(*) Notice: Subject to any disclaimer, the term of this patent is extended or adjusted under 35 U.S.C. 154(b) by 60 days.

(21) Appl. No.: 10/404,033

(22) Filed: Mar. 31, 2003

(65) Prior Publication Data
US 2003/0152998 A1 Aug. 14, 2003

Related U.S. Application Data

(62) Division of application No. 10/048,800, filed as application No. PCT/US98/27293 on Dec. 22, 1998, now Pat. No. 6,844,158.

(60) Provisional application No. 60/068,394, filed on Dec. 22, 1997, provisional application No. 60/071,627, filed on Jan. 16, 1998.

(51) Int. Cl.
C12Q 1/68 (2006.01)
C07H 21/02 (2006.01)

(52) U.S. Cl. .......................... 435/6; 536/23.1

(58) Field of Classification Search ............ 435/6; 536/23.1, 24.32
See application file for complete search history.

(56) References Cited

U.S. PATENT DOCUMENTS

| | | | |
|---|---|---|---|
| 4,906,561 A | 3/1990 | Thornthwaite | |
| 5,498,520 A * | 3/1996 | Chapman | 435/5 |
| 5,545,528 A | 8/1996 | Mitsuhashi et al. | 435/6 |
| 5,595,879 A | 1/1997 | Utermohlen | 435/6 |
| 5,652,141 A | 7/1997 | Henco et al. | 435/6 |
| 5,656,462 A * | 8/1997 | Keller et al. | 435/91.2 |
| 5,990,298 A | 11/1999 | Carmichael et al. | |
| 6,020,186 A | 2/2000 | Henco et al. | 435/6 |
| 6,277,648 B1 | 8/2001 | Colpan | 436/177 |
| 6,495,319 B1 | 12/2002 | McClelland et al. | |
| 6,844,158 B1 * | 1/2005 | Mitsuhashi | 435/6 |
| 2002/0010323 A1 | 1/2002 | Mitchell et al. | |
| 2002/0039783 A1 | 4/2002 | McMillan et al. | |
| 2003/0152998 A1 | 8/2003 | Mitsuhashi | |
| 2004/0072193 A1* | 4/2004 | Mitsuhashi | 435/6 |
| 2004/0265864 A1* | 12/2004 | Mitsuhashi | 435/6 |

FOREIGN PATENT DOCUMENTS

| | | |
|---|---|---|
| EP | 0 487 028 A2 | 5/1992 |
| EP | 0 726 310 A1 | 8/1996 |
| EP | 0 814 156 A2 | 12/1997 |
| JP | 04187077 A | 7/1992 |
| WO | WO/93/09250 | 5/1993 |
| WO | WO/93/15228 | 8/1993 |
| WO | WO95/00533 | 1/1995 |
| WO | WO95/02049 | 1/1995 |
| WO | WO 9502049 A1 * | 1/1995 |
| WO | WO9502049 A1 * | 1/1995 |
| WO | WO96/31622 | 10/1996 |
| WO | WO96/41810 | 12/1996 |
| WO | WO98 21321 | 5/1998 |
| WO | WO99 32654 | 7/1999 |

OTHER PUBLICATIONS

Itoh et al. Simple and rapid preparation of plasmid template by filtration method using microtiter filter plate. Nucleic Acids Res., vol. 25, No. 6, pp. 1315-1316, Mar. 1997.*

A. Reyes-Engle, et al., Direct quantification of specific mRNA using a selected biotinylated oligonucleotide by free solution capillary electrophoresis, Nucleic Acids Research. 1993 vol. 21, No. 3 pp. 759-760.

Barbara Galvan, et al., Detection of Prostate-Specific Antigen mRNA by Reverse Transcription Polymerase Chain Reaction and Time-Resolved Fluorometry, Clinical Chemistry, 1995, vol. 41, No. 12, pp. 1705-1709.

Takashi Ishikawa, et al., Construction of cDNA bank from biopsy speciments for multiple gene analysis of cancer, Clinical Chemistry 1997, vol. 43, No. 5, pp. 764-770.

Promega Catalog, 1998, "PolyATtract Series 9600 mRNA Isolation System," p. 196.

Oroskar, A.A., et al., "Detection of Immobilized Amplicons by ELISA-Like Techniques," *Clinical Chemistry* American Association for Clinical Chemistry, Winston, US, vol. 42, No. 9, Sep. 1996, pp. 1547-1555, EX 009010506.

G. Lévesque, et al, "Reverse Transcription and PCR Amplification of Rare MRNAS Immobilized on Oligo(dT) Cellulose" *Academic Press*, San Diego, CA US., vol. 213, No. 1, Aug. 15, 1993; pp. 170-171 EP 000616664.

Y. Hamaguchi, et al., "Direct Reverse Transcription-PCR on oligo (dT)-immobilized polypropylene microplates after capturing total mRNA from crude cell lysates," *Clinical Chemistry* 44:11 (1998) pp. 2256-2263.

G. Nolasco, et al., "A method combining immunocapture and PCR amplification in a microtiter plate for the detection of plant viruses and subviral pathogens," *Journal of Virological Methods*, 45 (1993) 201-218.

(Continued)

Primary Examiner—Suryaprabha Chunduru
(74) Attorney, Agent, or Firm—Knobbe, Martens, Olson & Bear, LLP

(57) ABSTRACT

The entire process of reverse transcription-polymerase chain reaction (RT-PCR) is simplified by using oligonucleotide-immobilized microplates made of, e.g., polypropylene, to which oligonucleotides are securely immobilized and which can be subjected to thermal cycles of PCR. RT-PCR is preferably conducted in solid-phase. Capturing of mRNA and RT-PCR can be conducted in the same plates. The cDNA synthesized from the mRNA captured on the microplates can be used more than once. Further, in combination with the microplates, a filter plate is used for the preparation of cell lysates wherein target cells are placed on the filter plate, and a lysis buffer is passed through the cell layer on the filter to transfer cell lysate directly to the microplate via well-to-well communication.

2 Claims, 10 Drawing Sheets

OTHER PUBLICATIONS

Raineri I., et al. "Improved Efficiency For Single-sided PCR by Creating a Reusable Pool of First-strand cDNA coupled to a solid phase," *Nucleic Acids Research, Oxford University Press,* Surrey, GB, vol. 19, No. 14, Jul. 25, 1991; p. 4010, XP002023130.

A. Ruppert, et al., "A Filtration Method for Plasmid Isolation Using Microititer Filter Plates," *Analytical Biochemistry* 230, pp. 130-134 (1995).

N. C. Nicolaides, et al., "A Simple Efficient Method for the Separate Isolation of RNA and DNA From the Same Cells," *BioTechniques,* vol. 8, No. 2 (1990) pp. 154 and 156.

Fukuchi et al. DNA damage induces p 21 protein expression by inhibiting ubiquitination in ML-1 cells. Biochemica et Biophysica Acta. vol. 1404, pp. 405-411, 1998.

Joklik. Procedures for studying transcription and translation of viral and host nucleic acids in interferon-treated cells. Methods in Enzymology, vol. 79, pp. 307-330, 1981.

Matsuda K. et al. 2001 *High throughput methodology for measurement of newly expressed poly(A)+mRNA from nuclei, FASEB J* 15:A515.

Geneplate and Ribocap Customer Order From (1998) Advanced Gene Computing Technologies, Inc., 1 page.

Advanced Gene Computing Technologies, "RiboCap High thruoghput RT-PCR system" (1997).

Mitsuhashi, M. et al. "Gene manipulation on plastic plates", Nature, vol. 357, pp. 519-520 (1992).

Foley, K. et al., "Quantitation of RNA using the polymerase chain reaction", Trends in Genetics, vol. 9, p. 380-385 (1993).

Miura Y. et al., "Fluorometric determination of total mRNA with oligo(dT) immobilized on microtiter plates", Clin. Chem., vol. 42, pp. 1758-1764 (Nov. 1996).

Leno et al. "reactivation of DNA Replication in Nuclei from Terminally Differentiated Cells: Nuclear Membrane Permeabilization Is Required for Initiation in Xenopus Egg extract", Exp. Cell res., vol. 232, pp. 412-419 (1997).

Tominaga, K. et al., "Colorimetric ELISA measurement of specific mRNA on immobilized-oligonucleotide-coated microtiter plate by reverse transcription with biotinylated mononucleotides", Clin. Chem., vol. 42, pp. 1750-1757 (Nov. 1996).

* cited by examiner

METHOD OF PREPARING CELL LYSATE

RELATED APPLICATIONS

This application is a divisional application of U.S. application Ser. No. 10/048,800, filed Jan. 31, 2002 now U.S. Pat. No. 6,844,158, which is a National Phase Application under 35 U.S.C. § 371 of International Application No. PCT/US98/27293, filed on Dec. 22, 1998 and claims priority to U.S. Provisional Application No. 60/068,394 filed on Dec. 22, 1997 and U.S. Provisional Application No. 60/071,627 filed on Jan. 16, 1998.

BACKGROUND OF THE INVENTION

Polymerase chain reaction (PCR) following cDNA synthesis from mRNA (reverse transcription-polymerase chain reaction, RT-PCR) to analyze gene expression of any specific mRNA in cells and tissues has become common technique, because of its better sensitivity and less labor-intensive manipulations than the traditional Northern blot (Kawasaki E S, Wang A M, "Detection of gene expression. In: Erlich, E A. PCR technology", New York: Stockton, 1989; 89-97). Furthermore, because recently available recombinant Tth thermostable polymerase has activities of both reverse transcriptase and DNA polymerase, both steps can be performed simultaneously in a single tube without changing the buffer system (Myers T W, Gelfand D H, "Reverse transcription and DNA amplification by a Thermus thermophilus DNA polymerase", *Biochemistry* 1991; 30:7661-6). However, it still requires purification of total RNA or mRNA from cells and tissues, which takes additional time-consuming, and labor-intensive step(s).

It has been reported that mRNA is successfully captured by an oligo(dT)immobilized polystyrene (PS) microplate (GENEPLATE®, Hitachi Chemical Co., Japan, and AGCT, Irvine, Calif.) (Mitsuhashi M, et al., "Gene manipulation on plastic plates", *Nature* 1992:357:519-20, Miura Y, et al., "Fluorometric determination of total mRNA with oligo(dT) immobilized on microtiter plates", *Clin Chem* 1996:42: 1758-64, Miura Y, et al., "Rapid cytocidal and cytostatic chemosensitivity test by measuring total amount of mRNA", *Cancer Lett* 1997:116:13944) followed by single- and double-stranded cDNA synthesis on the plate (Tominaga K, et al., "Colorimetric ELISA measurement of specific mRNA on immobilized-oligonucleotide-coated microtiter plates by reverse transcription with biotinylated mononucleotides", *Clin Chem* 1996:42:1750-7). Once double stranded cDNA is formed on a PS microplate of GENEPLATE®, sense stranded cDNA can be removed and used as a template for multiple PCR experiments (Ishikawa T, et al., "Construction of cDNA bank from biopsy specimens for multiple gene analysis of cancer", *Clin Chem* 1997:43:764-70). Unfortunately, PCR cannot be performed on this PS microplate, because of its heat instability during the denaturing step in PCR cycles. Although heat stable polypropylene (PP) tubes and microplates are primary vessels for PCR, it is difficult to immobilize oligonucleotides onto a PP surface, because of its extremely chemically stable surface characteristics. However, oligo(dT)-immobilized polypropylene plates have recently become available.

As described above, RT-PCB is a very useful technology in various fields including diagnostic molecular pathology (Bortolin S, et al., "Quantitative RT-PCR combined with time-resolved fluorometry for determination of BCR-ABL mRNA", *Clin Chem* 1996:42:1924-9). However, there are many steps involved in the analysis of RT-PCR; collection of cells, purification of RNA/mRNA, cDNA synthesis, PCR, and quantitation of PCR products. In particular, the purification of intact RNA molecules is the critical first step for the successful RT-PCR, and this requires labor-intensive multiple manipulations to eliminate or inactivate endogenous or contaminated ribonuclease (RNase) in cells and tissues. Although recent PCR technologies allow researchers to continuously monitor the quantity of PCR products with various in-line or off-line verification procedures of amplified PCR products (Morris T, et al., "Rapid reverse transcription-PCR detection of hepatitis C virus RNA In serum by using the TaqMan fluorogenic detection system", *J Clin Microbiol* 1996:34:p2933-6, Wittwer C T, et al., "The Light-Cycler: A microvolume multisample fluorimeter with rapid temperature control", *BioTechniques* 1997:22:171-181), lack of a simplified RNA preparation system prevents full automation of RT-PCR.

SUMMARY OF THE INVENTION

In order to simplify the entire process of gene expression analysis, by using oligonucleotide-immobilized microplates to which oligonucleotides are securely immobilized and which can be subjected to thermal cycles of PCR (PCR microplates), capturing of mRNA and reverse transcription-polymerase chain reaction (RT-PCR) can be conducted on the same plates. Heretofore, microplates were never used for PCR due to insufficient thermal stability, and thus, RT-PCR processes were time-consuming and labor-intensive. In using PCR microplates such as those made of polypropylene, polyolefine, or polycarbonate, because of their fluorescent characteristics, immobilized oligonucleotide, hybridized mRNA, and synthesized cDNA are quantitated fluorometrically by using nucleic acid stain or enzymatically by producing fluorescence or chemiluminescence. The PCR microplates can also capture mRNA from crude cell lysates without purification of RNA or mRNA.

Although hybridized mRNA can be successfully used for one-step RT-PCR with rTth polymerase or two-step RT-PCR with reverse transcription followed by PCR, two-step RT-PCR exhibits surprisingly higher sensitivity than one-step RT-PCR. This is surprising because two-step RT-PCR requires an inefficient solid phase reverse transcription reaction, whereas one-step RT-PCR is conducted in a more efficient liquid phase reaction by first dissociating mRNA from the PCR microplates.

In addition, cDNA synthesized from mRNA captured by immobilized oligonucleotide on the PCR microplates can be used more than once, thereby amplifying plural times different or the same portions of the cDNA by using appropriate primers. This multiple-PCR system, wherein multiple PCRs are synthesized from the cDNA on the PCR microplates, is useful in basic research, diagnostics, and drug screening, with potential application to future automation.

Further, conventionally, cell lysate is prepared by vigorous homogenization processes which are not only time-consuming and labor-intensive, but also cause fluctuation of the amount of recovered mRNA. In the present invention, in combination with the PCR microplates, by placing target cells on a filter plane evenly and passing a lysis buffer through the cell layer on the filter without disturbing the cells, it is possible to drastically simplify the preparation of cell lysate and significantly stabilize the yield of recovered cytosolic RNA. It is very convenient if the microplate and the filter plate are available as a kit for direct RT-PCR. In the above, a lysis buffer, wash buffer, reagents for RT-PCR/PCR, and PBS are commercially available or can readily be prepared so that they need not be included in the kit. However, for convenience, a lysis buffer may be included in the kit for releasing cytosolic mRNA present in the cells when passing through the cell layer on the filter plate. In the above, the lysis buffer comprises a mild detergent for destructing cell membranes but maintaining nuclei to be intact and a reagent for inhibiting RNase activity or inactivating RNase, said lysis buffer having a pH and salt concentration for hybridization.

Because of the above features, the PCR microplates and filter plates can drastically and surprisingly simplify the entire process of RT-PCR from the preparation of cell lysate to measuring specific PCR products with high reliability. Thus, this technology is highly useful in various molecular analyses including basic research, diagnostics, and drug screening, with potential application to future automation.

DETAILED DESCRIPTION OF THE PREFERRED EMBODIMENT

PCR Microplates

Figure 1:
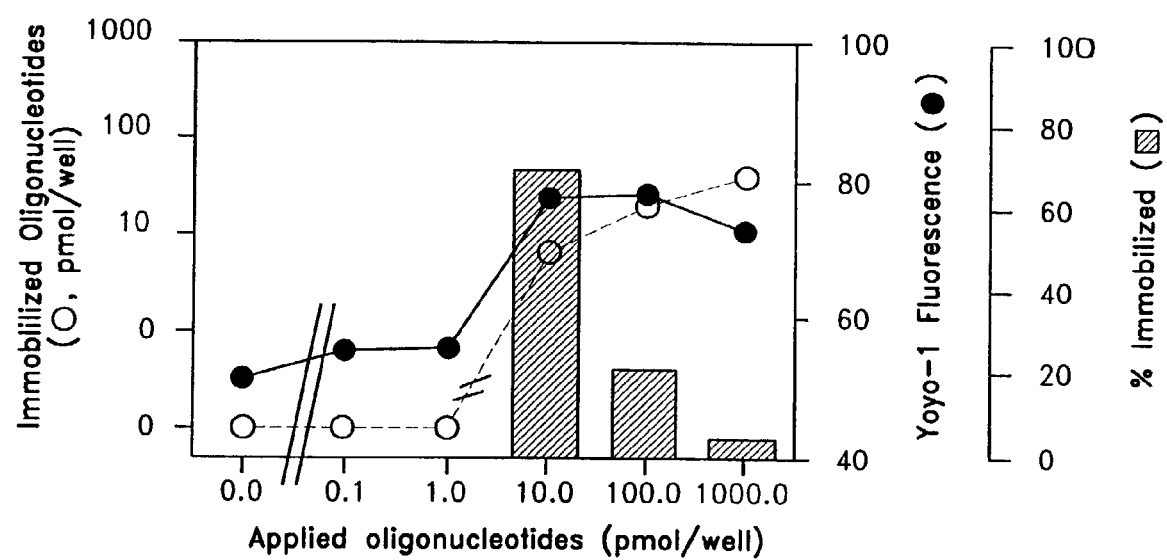
FIG. 1 is a graph showing quantities of oligo(dT) immobilized onto oligonucleotide-immobilized polystyrene/polyolefine microplates, indicating that approximately 69% of applied oligonucleotides (10 pmol) were immobilized onto the surface of the microplates.

In the present invention, oligonucleotide-immobilized microplates to which oligonucleotides are securely immobilized and which can be subjected to thermal cycles of PCR (PCR microplates) are used, wherein the capture of mRNA and reverse transcription-polymerase chain reaction (RT-PCR) can be conducted on the same plates. The PCR microplates can also capture mRNA from crude cell lysates without purification of RNA or mRNA. What makes PCR using microplates possible is the use of PCR microplates to which oligonucleotides are securely immobilized and which can be subjected to thermal cycles of PCR. For example, conventional oligonucleotide-immobilized polystyrene microplates such as GENEPLATE®(AGCT, Irvine, Calif.) cannot be used for PCR because polystyrene's heat stability is low. PCR microplates usable in the present invention include, but are not limited to, oligonucleotide-immobilized microplates made of polypropylene, polyolefine, or polycarbonate, and other microplates made of heat resistant polymer or resin which can be used in thermal cycles of PCR. In the above, polyolefine microplates may be preferred due to their surface characteristics allowing secure immobilization of oligonucleotides. Oligonuleotides immobilized on microplates include, but are not limited to, oligo(dT) and other oligonuleotides specific to mRNA or target RNA. Appropriate sequences can be identified by using HYB simulator™ software (AGCT, Irvine, Calif.) using hybridization simulation against GenBank primate database (Mitsuhashi M, et al., "Oligonucleotide probe design—a new approach", *Nature* 1994:367:759-61, Hyndman D, et al., "Software to determine optimal oligonucleotide sequences based on hybridization simulation data", *BioTechniques* 1996:20:1090-7). See also U.S. Pat. No. 5,556,749, issued Sep. 17, 1996 to Mitsuhashi M, et al., entitled "Oigo probe designstation: a computerized method for designing optimal DNA probes", which is incorporated hereby by reference herein. The amount of immobilized oligonucleotides can be as high as 10-100 pmol per well (normally 10-30 pmol).

Because of stable surface characteristics of polypropylene, oligonucleotides cannot be immobilized thereon easily. However, recently, some manufacturers produce PCR microplates for molecular biological applications, which can allow researchers to conduct high throughput PCR. In addition, a company such as Hitachi Chemical Research Center (Irvine, Calif.) can pretreat any commercially available PCR plates to allow oligonucleotides to be immobilized thereonto. Accordingly, this oligonucleotide-immobilized polypropylene (or polyolefine or polycarbonate) plate has recently become available (AGCT, Irvine, Calif.).

As compared with PS plates or tubes unsuitable for 94° C. heat denaturing step in PCR, PCR microplates can advantageously be used for PCR. Like widely used PCR microtubes in molecular biological experiments, PCR microplates have low capacity for nonspecific absorption of proteins and DNA/RNA, and resistance to organic chemicals (i.e. pheno/chloroform). These characteristics can be maintained even when oligonucleodites are immobilized thereonto.

Another advantage of oligonucleotide-immobilized PCR microplates is the strict specificity to mRNA, but not to rRNA, tRNA or DNA, eliminating the potential problem of false PCR amplification from contaminated genomic DNA, whereas cellulose or beads often contain detectable amounts of rRNA, tRNA and DNA. Furthermore, less variation among wells and plates, excellent stability, and availability of various quality control protocols make this technology very competitive.

Oligonucleotide-immobilized polystyrene microplates have been shown to exhibit a wide variety of applications, which include the capture of total and specific mRNA, ss-cDNA and ds-cDNA synthesis, quantitation of specific mRNA, and sense and antisense mRNA synthesis. Oligonucleotide-immobilized PCR microplates can also be used for the same purposes as PS microplates. See U.S. Pat. No. 5,656,462, issued Aug. 12, 1997 to Keller C, et al., entitled "Method for synthesizing polynucleotide immobilized support", which is incorporated hereby by reference herein.

An interesting feature of PCR microplates is their fluorescent characteristics. Although PCR plates are cloudy and not completely transparent compared to PS plates, fluorescence measurement of YOYO™-1 or equivalent dyes exhibited better performance in PCR microplates than in PS microplates (Ogura M, Mitsuhashi M, "Screening method for a large quantity of polymerase chain reaction products by measuring YOYO-1 fluorescence on 96-well polypropylene plates", *Anal Biochem* 1994:218:458.9). See also U.S. Pat. No. 5,545,528, issued Aug. 13, 1996 to Mitsuhashi M, et al., entitled "Rapid screening method of gene amplification products in polypropylene plates", which is incorporated hereby by reference herein. This allows for conducting various analysis quite easily. For example, the amounts of both immobilized oligonucleotides, i.e., captured mRNA and synthesized cDNA, can be determined fluorometrically without using radioactive materials.

Detection of Fluorescence

Because of the fluorescent characteristics of polypropylene, polyolefine, or polycarbonate plates, immobilized oligonucleotide, hybridized mRNA, synthesized cDNA, and PCR products are quantitated fluorometrically by using nucleic acid stain or enzymatically by producing fluorescence or chemiluminescence, e.g., ATTOPHOS™ or LUMIPHOS™. The nucleic acid stains include, but are not limited to, a fluorescent dye selected from the group consisting of 1,1'-(4,4,7,7-tetramethyl-4,7-diazaundecamethylene)-bis-4-[3-methyl-2,3-dihydro -(benzo-1,3-oxazole)-2-methylidene]-quinoliumetraiodide (YOYO™-1), 1,1'-(4,4,7,7-tetramethyl-4,7-diazaundecamethylene)-bis-4-[3-methyl-2,3-dihydro-(benzo-1,3-thiazole)-2-methylidene]-quinoliumetraiodide (TOTO™-1), 1,1'-(4,4,7,7,-tetramethyl-4,7-diazaundecamethylene)-bis-4-[3-methyl-2,3-dihydro-(benzo-1,3-thiazole)-2-propenylidene]-quinoliumetraiodide TOTO™-3), SYBR®-Green I, II, and PicoGreen®. See also U.S. Pat. No. 5,545,528 described above. Accordingly, this oligonucleotide-immobilized polypropylene, polyolefine, or polycarbonate plate has recently become available.

In the following experiments, as a oligonucleotide-immobilized PCR microplate, oligo(dT)-immobilized polypropylene/polyolefine microplate GENEPLATE®-PP (Hitachi Chemical Research Center, Irvine, Calif.) was used. However, oligonucleotide-immobilized PCR microplates are not limited to the above, and include any oligonucleotide-immobilized microplates to which oligonucleotides are securely immobilized and which can be subjected to thermal cycles of PCR.

Two-Step RT-PCR or Solid-Phase RT-PCR

There are roughly two ways to perform RT-PCR: one-step RT-PCR and two-step RT-PCR. In one-step RT-PCR, with rTth polymerase or optimal combination of reverse transcriptase and DNA polymerase (Titan™, one tube RT-PCR kit, Boehringer Mannheim, Indianapolis, Ind.), RT-PCR can be performed on the oligonucleotide-immobilized PCR microplate without changing the buffer. As another one-step RT-PCR, after capturing mRNA by hybridization of mRNA and immobilized oligo(dT), mRNA is removed to a RT-PCR buffer, and RT-PCR can be performed. In contrast, in two-step RT-PCR, after hybridization on oligonucleotide-immobilized PCR microplates, captured mRNA is reverse transcribed to cDNA on the same microplates, reactants are removed by aspiration, and PCR is conducted by using heat stable DNA polymerase, e.g., either rTth or Taq polymerase with an appropriate buffer. In the above, PCR is conducted in a thermal cycler with, e.g., 60 cycles of 94° C. denaturation for 1 min, 60° C. annealing for 1 min followed by 72° C. extension for 1 min, by using the same oligonucleotide-immobilized PCR microplates as used for hybridization. It is believed that one of ordinary skill in the art expects that one-step or liquid-phase RT-PCR is better than two-step RT-PCR with respect to PCR efficiency. However, surprisingly, when PCR is conducted from synthesized cDNA on the oligonucleotide-immobilized PCR microplates (two-step RT-PCR), RT-PCR can be approximately 10,000-fold more sensitive than conventional one-step RT-PCR, and transcript can be detected from cell lysates containing only 100 cells. This is very surprising because two-step RT-PCR requires inefficient solid phase reverse transcription reaction, whereas one-step RT-PCR is conducted in more efficient liquid phase reaction by first dissociating mRNA from the oligonucleotide-immobilized PCR microplates. One explanation may be as follows: It is believed that primers are used for dimer formation during reverse transcription. More primer dimers are formed in one-step PCR than two-step RT-PCR. Although hybridization efficiency is lower in two-step RT-PCR than one-step RT-PCR, primer dimers formed during initial reverse transcription phase exist throughout PCR in two-step RT-PCR, thereby drastically increasing RT-PCR sensitivity.

Reamplification by Immobilized cDNA (Multiple-PCR System)

cDNA synthesized from mRNA captured by immobilized oligonucleotide on the oligonucleotide-immobilized PCR microplate can be used more than once, i.e., cDNA on the oligonucleotide-immobilized PCR microplate is quite stable. This interesting feature allows reamplification by the same immobilized cDNA to amplify plural times different or the same portions of the cDNA of interest by using appropriate primers. This multiple-PCR system, wherein multiple PCRs are synthesized from the cDNA on the oligonucleotide-immobilized PCR microplates, is useful in basic research, diagnostics, and drug screening, with potential application to future automation.

High Throughput RT-PCR System

Conventionally, cell lysate is prepared by disrupting cells with a lysis buffer to release cytosolic mRNA, followed by centrifugation. Supernatants are used for hybridization. This vigorous homogenization process is not only time-consuming and labor-intensive, but also causes fluctuation of the amount of recovered mRNA. By placing cells on a filter membrane evenly and passing a lysis buffer through the cell layer on the filter membrane without mechanical homoginization of the cells, it is possible to drastically simplify the preparation of cell lysate and significantly stabilize the yield of recovered cytosolic RNA.

Namely, in the present invention, in order to simplify the entire RT-PCR process starting from cells on culture plates, cells are transferred to a filter plate and cells are trapped onto its membrane by vacuum aspiration, positive pressure, or centrifugation. The filter plate is then assembled on top of a oligonucleotide-immobilized PCR microplate having plural wells, and Lysis buffer is added to each well to mildly destruct cell membranes. After these two-plate sandwiches are centrifuged, cell lysate containing cytosolic mRNA are transferred to the oligonucleotide-immobilized PCR microplate for hybridization. After hybridization at room temperature for 1 hour, for example, RT-PCR can be conducted in automated instrument. In the above, a filter or membrane of the filter plate includes, but is not limited to, glass fiber, polypropylene or polyolefine mesh, wool, and other membranes which have a pore size such that target cells can be trapped without any leakage of cells from the membrane, but cytosolic mRNA can pass therethrough. For example, using glass fiber (Grade 934AH, Cambridge Technology, Inc. Watertown, Mass.) or Whatman GF/F grade glass fiber memberane, most of cultured cells and blood leukocyte can be trapped. In the above, glass fiber plates are preferable. Further, because the filter plate is mounted on the top of a oligonucleotide-immobilized PCR microplate, the configuration of the filter plate needs to correspond to that of the oligonucleotide-immobilized PCR microplate with respect to, e.g., the number of wells wherein the wells of the filter plate are communicated with the respective wells of the oligonucleotide-immobilized PCR microplate when subjected to centrifugation. The maximum capacity of cells per well is normally $10^4$ to $10^7$.

In the above, the cell lysate can be passed through the membrane of the filter plate with the aid of force generated by means of centrifugation, vacuum, or positive pressure. The force necessary to pass the cell lysate through the membrane is easily determined by simple experiments.

In the above, the lysis buffer comprises a detergent for destructing cell membranes, RNase inhibitor for inhibiting RNase activity or deactivating or destroying RNase, and pH control agent and salt for hybridization. In the above, RNase must be active in the lysis buffer. Further, in order to mildly destruct cell membranes so as to prevent contamination of nucleus, the use of a mild detergent is preferable (e.g., NP-40 or TRITON™-X). The above-described lysis buffer is useful and can be used for oligonucleotide-immobilized PCR microplates without the use of filter plates.

The protocols of this system include, but are not limited to, the following:

Step 1: Transfer Cells from Culture Plate to Filter Plate

1. Place a filter plate onto a vacuum manifold.
2. Transfer cells from culture plates to the filter plate by using, e.g., multi-channel pipettes.
3. Vacuum aspirate the filter plate to trap cells onto membranes.
4. Wash each well once or twice with, e.g., 50 µl each of PBS (optional).

Step 2: Transfer Cell Lysate from Filter Plate to Oligonucleotide-Immobilized PCR Microplate for Hybridization 1. Remove the filter plate from the vacuum manifold and place it on top of the oligonucleotide-immobilized PCR microplate.

2. Add, e.g., 50 µl of lysis buffer 10 mM Tris, pH 8.0, 1 mM EDTA, 0.5 M NaCl, 0.5% NP-40, 20 mM vanadyl ribonucleoside complex, RNase-free), and centrifuge at, e.g., 1,500×g for 10 min.

3. Incubate the oligonucleotide-immobilized PCR microplate at room temperature for 1 hour for hybridization between immobilized oligo(dT) and poly(A) tails of mRNA present in cytosolic fraction of cells.

Step 3: RT-PCR and Post-PCR Analysis

1. Wash each well once or twice with, 50 µl of wash buffer (e.g., 10 mM Tris, pH 8.0, 1 mM EDTA, 0.3 M NaCl, RNase-free).

2. Start RT-PCR and monitor the amount of PCR products in an automated PCR instrument.

According to the present invention, a rapid, inexpensive, high throughput, and easily automated method for the entire RT-PCR process starting from cells can be realized.

Philadelphia chromosome (Ph[1]) found frequently in chronic myelogenous leukemia (CML) is a reciprocal translocation of ABL protooncogene from chromosome 9 to a portion of the BCR gene in chromosome 22 [t(9;22)(q34; q11)] (Wehnert M S, at al., "A rapid scanning strip for triand dinucleotide short tandem repeats", Nucleic Acids Res 1994: 22:1701-4). Specific RT-PCR amplification of BCR-ABL mRNA from peripheral blood cells or bone marrow cells provides a highly sensitive and quantitative methodology for the detection of residual leukemic cells. Because the detection of residual leukemic cells is one of critical indicators for the treatments of CNE, RT-PCR test of BCR-ABL mRNA is widely available in many institutions. However, in many cases, total RNA or mRNA is first purified from cell suspension. Using the present system, once cell lysates are applied to the oligonucleotide-immobilized PCR microplates for hybridization, one can proceed with not only direct RT-PCR described here, but also YOYO™-1quantitation of total amounts of mRNA (Miura Y, et al., Clin Chem 1996: 42:175-864), which may provide additional means of normalization or quality control of tested materials. Because of its simplicity and fluorescent characteristics, oligonucleotide-immobilized PCR microplates may be accepted as a platform for various molecular analyses including basic research, diagnostics, and drug screening, with potential application to future automation, especially in combination with filter plates.

EXAMPLES

The invention will be further explained with reference to Examples shown below. Materials and methods used in the Examples are as follows:

Materials: Oligo(dT)-immobilized oligonucleotide-immobilized PCR microplates (GENEPLATE®-PP, Hitachi Chemical Research Center, Irvine, Calif.), YOYO™-1 (1,1'-(4,4,7,7-tetramethyl-4,7-diazaundecamethylene)-bis-4-[3-methl-2,3-dihydro-(benzo-1,3-oxazole)-2-methylidene]-quinoliumetraiodide, Molecular Probes, Eugene, Oreg.), reagents for PCR (Taq polymerase, EZ rTth RNA-PCR kit) (Perkin Elmar, Foster City, Calif.), K562 cell line (American Type Culture Collection, Rockville, Md.), 100 bp DNA ladder, phosphate buffered saline (PBS), vanadyl ribonucleoside complex (VRC), rabbit globin mRNA, cell culture medium and appropriate antibiotics, buffer-saturated phenol (Gibco-BRL, Geithersburg, Md.), fetal bovine serum (FBS, HyClone, Logan, Utah), biotin-dUTP (Clontech, Palo Alto, Calif.), ATTOPHOS™ (alkaline phosphatase substrate, JBL Scientific, San Luis Obispo, Calif.), cd4465 DNA (Genome Systems, St. Louis, Mo.) were purchased from the designated suppliers. RNA preparation reagents for MAGEXTRACTOR™ were kindly provided by Toyobo (Osaka, Japan). All other chemicals were purchased from Sigma (St. Louis, Mo.).

Cell culture: K562 cells were grown in RPMI 1640 containing 10% FBS, 500 units/ml penicillin, 500 µg/ml streptomycin, and subcultured twice a week at a ratio of approximately 1:10. Cell viability was assessed by the exclusion of trypan blue, and was always more than 95%.

Preparation of cell lysate and total RNA: Cells were washed with PBS twice, and suspended in lysis buffer (10 mmol/L Tris, pH 7.6, 1 mmol/L EDTA, 0.1% NP-40 and 20 mmol/L VRC) on ice for 5 min to release cytosolic mRNA as previously described (Miura Y, et al., *Clin Chem* 1996: 42:1758-64). Samples were then centrifuged at 15,000×g at 4° C. for 5 min, and supernatants were applied to GENE-PLATE®-PP for hybridization. In some experiments, cells were suspended in VRC-free lysis buffer, and immediately treated with an equal volume of phenol/chloroform twice to absorb proteins and nucleases. Deproteinated solutions were then subjected to hybridization.

When a glass fiber filter plate having 96 wells, adapted to be placed on the top of the microplates, was used to recover RNA, the above vigorous homogenization process was entirely omitted. Culture cells were transferred to the glass fiber filter plate by using multichannel pipettes (described later).

Total RNA was prepared by automated instrument (MAGEXTRACTOR™ MFX-2000, Toyobo, Osaka, Japan). In brief, cell pellets were suspended in kit-supplied caotropic agents, and placed in MAGEXTRACTOR, where RNA was absorbed to the surface of silica felite particles followed by magnet separation. RNA was then automatically eluted to 40 µl of low salt buffer, and was stored at −80° C. in a freezer until use. The final RNA was analyzed by agarose gel electrophoresis to confirm 18s and 28s rRNA bands.

Primer design and synthesis: Primers for cd4465 (sense: 5'-agtttcggagcggatgaatgc-3' (SEQ ID NO: 1), antisense: 5'-ggggcatcagaattttggttga-3' (SEQ ID NO: 2)), rabbit globin mRNA (sense: 5'-cgtggagaggatgttcttgg-3' (SEQ ID NO: 3), antisense: 5'-aacgatatttggaggtcagcac-3' (SEQ ID NO: 4)) and bcr-abl (sense: 5'-gaccaactcgtgtgtgaaactcca-3' (SEQ ID NO: 5), antisense: 5'-aaagtcagatgctactggccgct-3' (SEQ ID NO: 6)) were designed by HYB simulator™ software (AGCT, Irvine, Calif.) using hybridization simulation against GenBank primate database {Mitsuhashi M, et al., *Nature* 1994:367:759-61, Hyndman D, et al., *BioTechniques* 1996:20:1090-7). In the case of bcr-abl, the sense primer was located at bcr exon 2 and the antisense primer was located at abl exon 2. Primers were synthesized by DNA synthesizer (380B, Applied Biosystem, Foster City), according to the manufacturer's protocol.

One-Step RT-PCR: Template DNA/RNA, 300 µmol/L each of dATP, dGTP, dCTP and dTTP, 1×EZ buffer, 2 mmol/L Mn(OAc)$_2$, 0.5 µmol/L each of primer, and 0.1 µl rTth polymerase were mixed in a final volume of 5-50 µl, and overlayered with one drop of nuclease free mineral oil (Sigma). PCR was conducted in a thermal cycler (MJ Research, Watertown, Mass.) with 1 cycle of reverse transcription at 60° C. for 30 min and 94° C. denaturation for 1 min, followed by 40 cycles of 60° C. annealing/extension for 1 min and 94° C. of denaturation for 1 min. After PCR was completed, PCR products were analyzed by a 2.0% agarose gel electrophoresis with 0.5 µg/ml ethidium bromide in an electrophoresis chamber. Photographic images were recorded on Polaroid films (667, Cambridge, Mass.).

Two-Step RT-PCR: After hybridization, captured mRNA was reverse transcribed to cDNA by replacing biotin-dUTP with 10 mmol/L dTTP. Reactants were removed by aspiration, and PCR was conducted by using either rTth or Taq polymerase. For PCR with Taq polymerase, the buffer contained 1×buffer, 1.25 mmol/L MgCl$_2$, 300 µmol/L each of dATP, dGTP, dCTP and dTTP, 0.5 µmol/L each of primer, and 0.5 µl Taq polymerase in a final volume of 10-50 µl. PCR was conducted in a thermal cycler (MJ Research) with 60 cycles of 94° C. denaturation for 1 min, 60° C. annealing for 1 min followed by 72° C. extension for 1 min.

Experiment 1: Quantitation of Immobilized Oligonucleotides

GENUNC™ PP microplates (Nunc, Naparville, Ill.) treated at Hitachi Chemical Research Center, Irvine, Calif., were obtained from AGCT, Irvine, Calif., and oligonucleotides were immobilized thereonto. Oligonucleotide concentrations were determined before and after immobilization as 1.0 OD$_{260}$ unit equals to 30 µg/ml, and the amounts of immobilized oligonucleotides were calculated by subtracting one value from another. In separate experiments, YOYO-1 was diluted in TE (10 mmol/L Tris, pH 8.0, 1 mmol/L EDTA) in a final dilution of 1:1000, and applied to GENEPLATE®-PP microplates. The fluorescence was determined by CYTOFLUOR™ 2300 (Millipore, Bedford, Mass.) with excitation and emission wavelengths of 485 nm (bandwidth 20 nm) and 530 nm (band width 25 nm), respectively, as previously described (Miura Y, at al., *Clin Chem* 1996:42:1758-64, Miura Y, et al., *Cancer Lett* 1997: 116:139-44).

FIG. 1 is a graph showing quantities of oligo(dT) immobilized onto the oligonucleotide-immobilized PCR microplates. Oligonucleotide concentrations were determined before and after immobilization as 1.0 OD$_{260}$, and the amounts of immobilized oligonucleotides were calculated by subtracting one value from another (○). In parallel experiments, 1:1000 dilution of YOYO-1 was added to each well and its fluorescence was determined (●). Bars indicate the % immobilization from applied oligo(dT)$_{20}$. Each data point was the mean from triplicate determinations. Although the oligonucleotide-immobilized PCR microplates were opaque and not transparent compared to conventional PS plates, as shown in FIG. 1 (●), the fluorescence of the oligonucleotide-immobilized PCR microplates was significantly increased and reached a plateau when more than 10 pmol of oligonucleotides were applied. In further quantitating the actual amounts of immobilized oligonucleotides on the oligonucleotide-immobilized PCR microplates, as shown in FIG. 1 (○), 21.1 pmol of oligonucleotides were immobilized after 100 pmol of oligonucleotides were applied to each well. The amounts of immobilized oligonucleotides were saturated to 10-20 pmol, when more than 10 pmol of oligonucleotides were applied. Approximately 69% of applied oligonucleotides (10 pmol) were immobilized onto the surface of the microplates (FIG. 1, bar graph).

Experiment 2: mRNA Specificity of Oligonucleotide-Immobilized PCR Microplates

Figure 2:
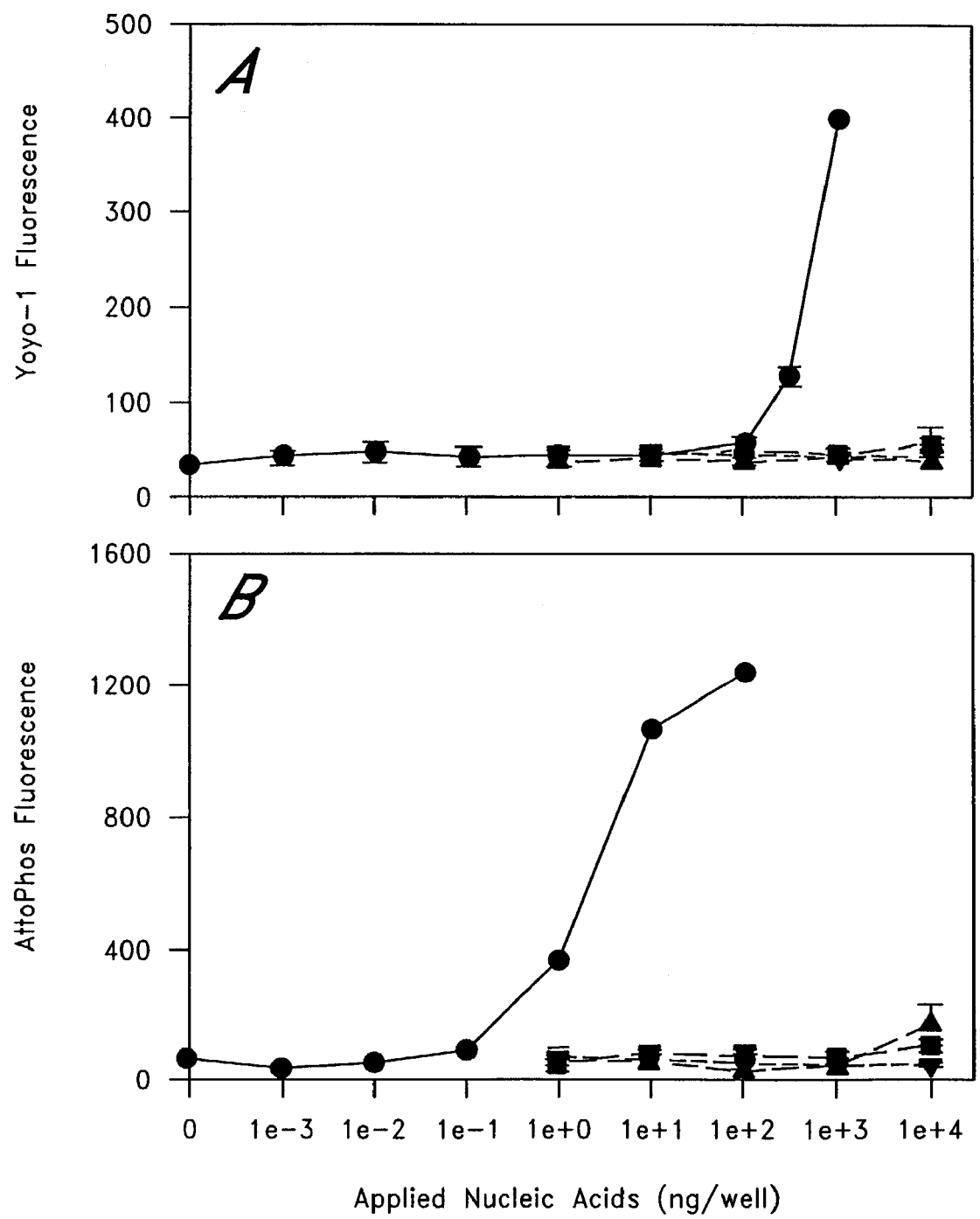
FIG. 2A is a graph showing mRNA specificity of the PCR microplates, wherein YOYO-1 fluorescent intensity indicates high specificity to mRNA (●) over DNA (■), rRNA (Δ), and tRNA (∇).
FIG. 2B is a graph showing mRNA specificity of the PCR microplates, wherein alkaline phosphatase substrate (ATTOPHDS™) indicates high specificity to mRNA (●) over DNA (■), rRNA (Δ), and tRNA (∇).

The next series of experiments was conducted to show mRNA specificity. FIG. 2A is a graph showing mRNA specificity of the oligonucleotide-immobilized PCR microplates, wherein YOYO-1 fluorescent intensity indicates high specificity to mRNA (●) over DNA (■), rRNA (Δ), and tRNA (∇). FIG. 2B is a graph showing mRNA specificity of the oligonucleotide-immobilized PCR microplates, wherein substrate ATTOPHOS™ indicates high specificity to mRNA (●) over DNA (■), rRNA (Δ), and tRNA (∇).

In the figures, various concentrations of rabbit globin mRNA (●), DNA (■), rRNA (Δ), tRNA (∇) were suspended in 50 μl of hybridization buffer (10 mmol/L Tris, pH 8.0, 1 mmol/L EDTA, 0.5 M NaCl) and applied to the well of the oligonucleotide-immobilized PCR microplates. After hybridization at room temperature for 1 hour, each well was washed once with hybridization buffer. In FIG. 2A, YOYO™-1 was diluted in TE (10 mmol/L Tris, pH 8.0, 1 mmol/L EDTA) in a final dilution of 1:1000, and applied to each well, and the fluorescence was determined by CYTOFLUOR™ 2300. In FIG. 2B, each well was resuspended in 50 μl of cDNA synthesis buffer (50 mmol/L Tris, pH 8.3, containing 75 mmol/L KCl, 3 mmol/L MgC12, 10 mmol/L DTT, 10 mmol/L each of dATP, dGTP, dCTP, 250 μmol/L biotin-dUTP, and 400 U of MMLV reverse transcriptase), and incubated at 37° C. for 1 hour. After each well was washed three times with wash buffer (10 mmol/L Tris, pH 7.6, containing 300 mmol/L NaCl and 10 mmol/L Tween 20), 50 μl of wash buffer containing 1:1000 dilution of streptavidin-alkaline phosphatase conjugates and incubated at room temperature for 30 min. After each well was washed three times with wash buffer, 50 μl of substrate (ATTOPHOS™) was added and incubated at room temperature for 20 min. The reaction was terminated by adding an equal volume (50 μl) of 100 mmol/L EDTA, and the fluorescence was determined by CYTOFLUOR™ 2300. Each data point was the mean±S.D. from triplicate determinations.

As shown in FIG. 2A, significant YOYO™-1 fluorescence was obtained from the wells where more than 100 ng of mRNA was applied, whereas YOYO™-1 fluorescence was not increased in the wells of rRNA, tRNA and DNA even when as many as 10 μg was applied. The specificity of quantitative cDNA synthesis on the oligonucleotide-immobilized PCR microplates was also tested as described above. As shown in FIG. 2B, significant ATTOPHOS™ fluorescence was obtained from the well where more than 0.1 ng/well of mRNA was applied, but not from the wells of rRNA, tRNA and DNA even when as many as 10 μg was applied.

Experiment 3: Quantitation of Hybridization

Figure 3:
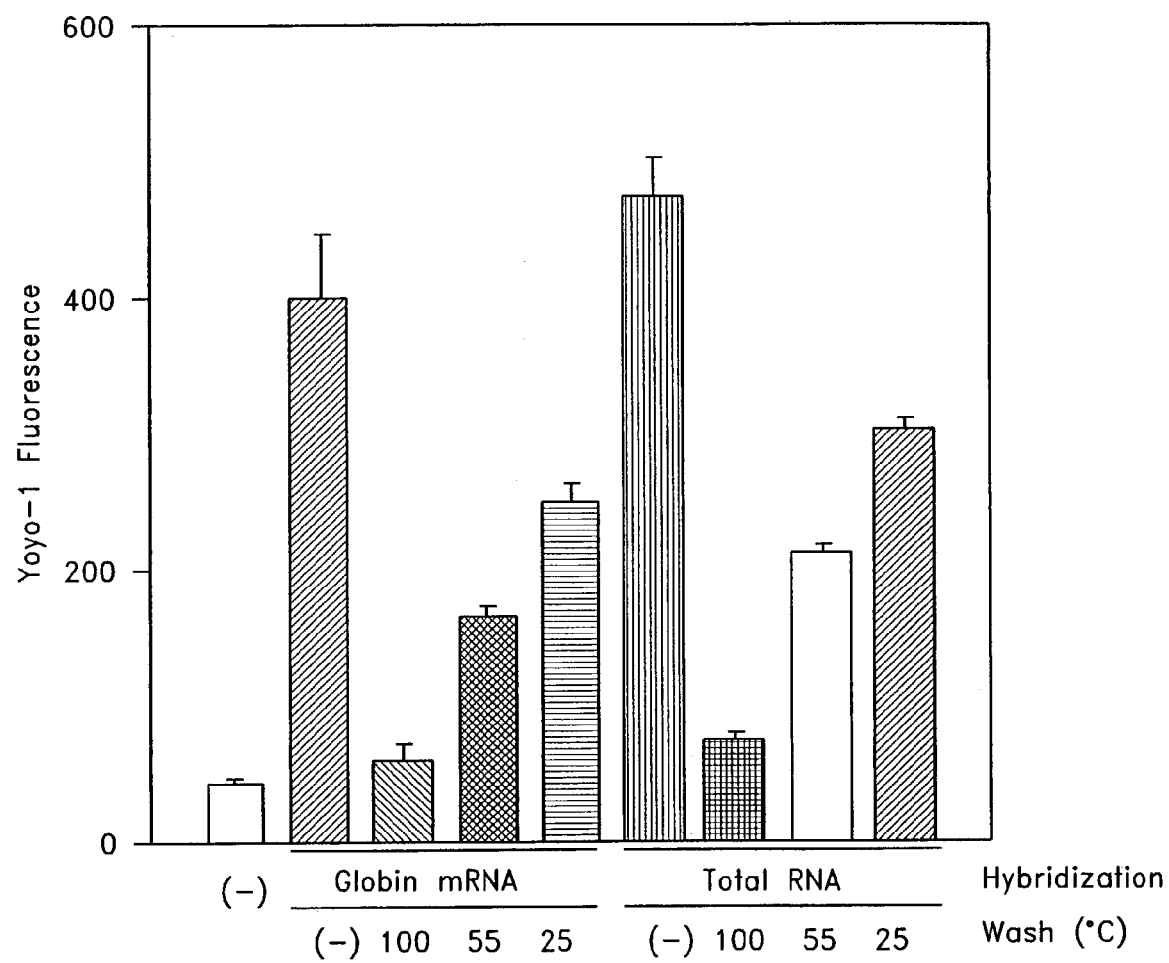
FIG. 3 is a graph showing reversible hybridization of mRNA on the PCR microplates, wherein YOYO-1 fluorescent intensity indicates sufficient reversibility of mRNA hybridization.

FIG. 3 is a graph showing reversible hybridization of mRNA on the oligonucleotide-immobilized PCR microplates. One μg of rabbit globin mRNA or 20 μg of total liver RNA was suspended in 50 μl of hybridization buffer and applied to the well of the oligonucleotide-immobilized PCR microplates. After hybridization at room temperature for 1 hour, wells were washed three times with DEPC water at different temperatures (25° C., 55° C. or boiling). YOYO™-1 was then applied to each well, and the fluorescence was determined by CYTOFLUOR™ 2300 as described above (Miura Y, et al., *Clin Chem* 1996:42:1758-64). Each data point was the mean±S.D. from triplicate determinations. As shown in FIG. 3, YOYO™-1 fluorescence was reduced to the basal levels by adding boiling DEPC water.

Experiment 4: Capacity of Hybridization

Moreover, in order to assess the hybridization capacity, various amounts of globin mRNA, total liver RNA or cell lysates were applied to the oligonucleotide-immobilized PCR microplates for hybridization. Hybridized mRNA was then recovered from the plates by adding boiling water, and a buffer (concentration was adjusted) was applied to fresh oligonucleotide-immobilized PCR microplates for the second hybridization. In parallel experiments, known concentrations of globin mRNA were also applied as a control. The quantitative cDNA synthesis described below was then conducted, and the amount of mRNA in the solutions was determined based on the values of standard globin mRNA. The amounts of cDNA synthesis were quantitated according to the protocol published by Tominaga et al. (*Clin Chem* 1996:42:1750-7) with minor modification. In brief, the mRNA-hybridized oligonucleotide-immobilized PCR microplate was resuspended in 50 μl of cDNA synthesis buffer (50 mmol/L Tris, pH 8.3, containing 75 mmol/L KCl, 3 mmol/L MgCl$_2$, 10 mmol/L DTT, 10 mmol/L each of dATP, dGTP, dCTP, 250 μmol/L biotin-dUTP, and 400 U of MMLV reverse transcriptase), and incubated at 37° C. for 1 hour. After each well was washed three times with wash buffer (10 mmol/L Tris, pH 7.6, containing 300 mmol/L NaCl and 10 mmol/L Tween 20), 50 μl of wash buffer containing 1:1000 dilution of streptavidin-alkaline phosphatase conjugates was added and incubated at room temperature for 30 min. After each well was washed three times with wash buffer, 50 μl of substrate (ATTOPHOS™, 1× concentration) was added and incubated at room temperature for 20 min. The reaction was terminated by adding an equal volume (50 μl) of 100 mmol/L EDTA, and fluorescence was determined by CYTOFLUOR™ 2300 (Millipore) with excitation and emission wavelengths of 485 nm (bandwidth 20 nm) and 560 nm (band width 25 nm), respectively.

As shown in Table I, approximately 50-65% of applied globin mRNA was hybridized to the plates. Applied globin mRNA did not saturate the plates even when 500 ng was used; 500 ng of globin mRNA equals approximately 1-2 pmol compared to 21 pmol of immobilized oligonucleotides. Moreover, approximately 34-48% of total RNA or cell lysates were captured by the plates when mRNA concentration was low, whereas high concentrations decreased capture efficiency, probably because of inefficient hybridization due to high viscosity.

TABLE I

| Applied | Amounts of total mRNA | Compared mRNA (means ± S.D., n = 3) | % Capture |
|---|---|---|---|
| globin mRNA | | | |
| 500 ng | 500 ng | 326.7 ± 47.3 ng | 65.3% |
| 50 ng | 50 ng | 32.0 ± 5.6 ng | 64% |
| 5 ng | 5 ng | 2.5 ± 0.3 ng | 50% |
| liver RNA | | | |
| 50 μg | 583 ng | 45.6 ± 14.2 ng | 7.8% |
| 5 μg | 58.3 ng | 14.8 ± 5.2 ng | 25.4% |
| 0.5 μg | 5.83 ng | 2.8 ± 0.3 ng | 48.0% |
| K562 cells | | | |
| 10$_5$ cells | 24.3 ng | 4.2 ± 0.9 ng | 17.2% |
| 10$_4$ cells | 2.43 ng | 0.83 ± 0.3 ng | 34.1% |

As shown above, the plates are not saturated even when as much as 500 ng of mRNA is applied, which also represents approximately 500 μg of total RNA or 10$^7$ cells per small surface area of 96 well plates. This is more than enough for the majority of experiments.

Experiment 5: RT-PCR in Oligonucleotide-Immobilized PCR Microplates

Human K562 leukemic cells, which express the b3a2 transcript from the Ph[1] translocation, were lysed with lysis buffer followed by centrifugation to remove cell debris and nuclear DNA. The supernatant containing cytosolic mRNA was then applied to the oligonucleotide-immobilized PCR microplates for hybridization. After 1 hour of hybridization at room temperature, unbound materials were removed by washing with hybridization buffer twice, and RT-PCR was started in the same wells.

Figure 4C:
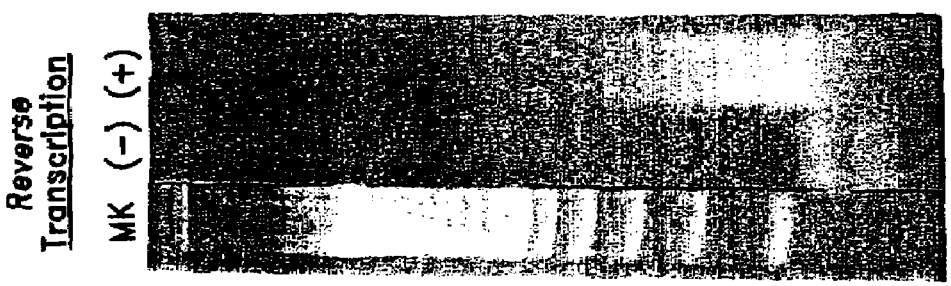
FIG. 4C shows the results of agarose gel electrophoresis showing PCR conducted with or without reverse transcription.
Figure 4B:
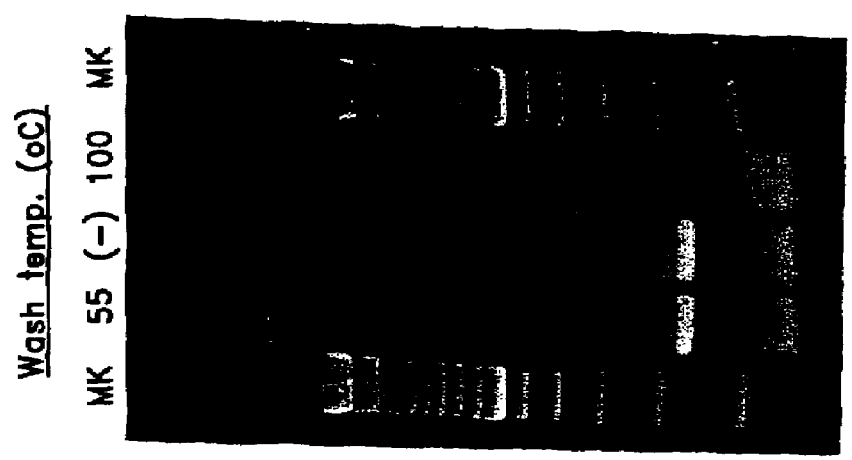
FIG. 4B shows the results of agarose gel electrophoresis showing insignificant false PCR from contaminated genomic DNA in the plates, wherein the band disappeared after being washed with boiling DEPC (diethylpyrocarbonate) water, but not after being washed with 55° C. DEPC water.
Figure 4A:
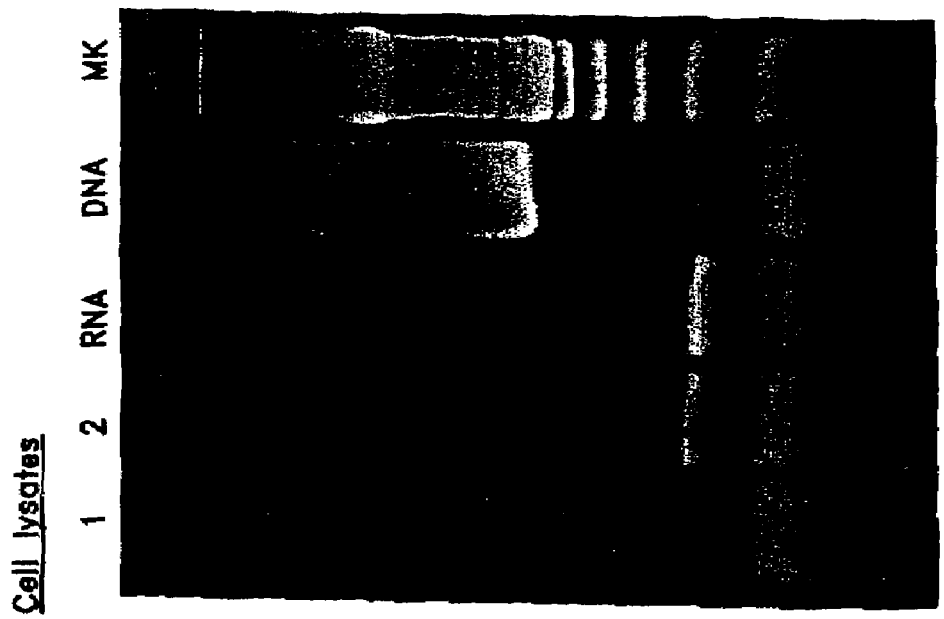
FIG. 4A shows the results of agarose gel electrophoresis showing RT-PCR products from the captured mRNA in crude cell lysates with the expected size of 168 base pairs.

That is, in FIG. 4A, $10^8$ K562 cells were suspended in lysis buffer (10 mmol/L Tris, pH 7.6, 1 mmol/L EDTA, 0.1% NP-40 and 20 mmol/L VRC) on ice for 5 min to release cytosolic mRNA. Samples were then centrifuged at 15,000×g at 4° C. for 5 min, and supernatants were applied to the oligonucleotide-immobilized PCR microplates for hybridization (lane 1). In lane 2, cells were suspended in VRC-free lysis buffer, and immediately treated with an equal volume of phenol/chloroform twice to absorb proteins/nucleases. Deproteinated solutions were then subjected to hybridization. In lane 3, total RNA was prepared by automated instrument as described in the Methods. After hybridization, RT-PCR was conducted in a thermal cycler with 1 cycle of reverse transcription at 60° C. for 30 min and 94° C. denaturation for 1 min, followed by 40 cycles of 60° C. annealing/extension for 1 min and 94° C. of denaturation for 1 min, as described in the Methods. Lane 4 was a control cd4465 DNA.

As shown in FIG. 4A (lane 1), BCR-ABL transcript was successfully amplified from the captured mRNA in crude cell lysates with the expected size of 168 base pairs. The size of PCR products was identical to that of PCR products from purified total RNA in the same cells (FIG. 4A, lane 3). Phenol/chloroform treated cell lysates exhibited thicker PCR products than VRC-containing cell lysates (FIG. 4A, lane 2).

In order to analyze the false PCR from contaminated genomic DNA in the plates, mRNA was removed by 55° C. or boiling DEPC water and one-step RT-PCR was conducted. That is, in FIG. 4B, after total RNA was hybridized, wells were washed with 55° C. DEPC water or boiling DEPC water 3 times, and one-step RT-PCR was conducted. As shown in FIG. 4B, PCR products of BCR-ABL transcript when washed with disappeared when wells were washed with boiling water, but not when washed with 55° C. water. These results were comparable to that of FIG. 3.

In separate experiments, PCR was conducted with or without reverse transcription. That is, in FIG. 4C, after total RNA was hybridized, cDNA was synthesized in one tube (+) and one tube was left without reverse transcription (−). PCR was then conducted with Taq polymerase in the presence of 1.25 mM $MgCl_2$ with 60 cycles of 94° C. denaturation for 1 min, 60° C. annealing for 1 min followed by 72° C. extension for 1 min. PCR products were separated by 2.0% agarose gel electrophoresis followed by staining with ethidium bromide. Mk indicates a 100 bp ladder. As shown in FIG. 4C, PCR products of BCR-ABL transcript were not amplified from the wells of negative reverse transcription even under low stringent conditions with a higher Mg concentration, whereas significant amounts of PCR products were obtained from the wells of positive reverse transcription.

In view of the foregoing, an advantage of the oligonucleotide-immobilized PCR microplates is the strict specificity to mRNA, but not to rRNA, tRNA or DNA (FIGS. 2A, 2B, 4A, 4B, 4C), eliminating the potential problem of false PCR amplification from contaminated genomic DNA, whereas cellulose or beads often contain detectable amounts of rRNA, tRNA and DNA.

Experiment 6: Two-Step RT-PCR

Figure 5A:
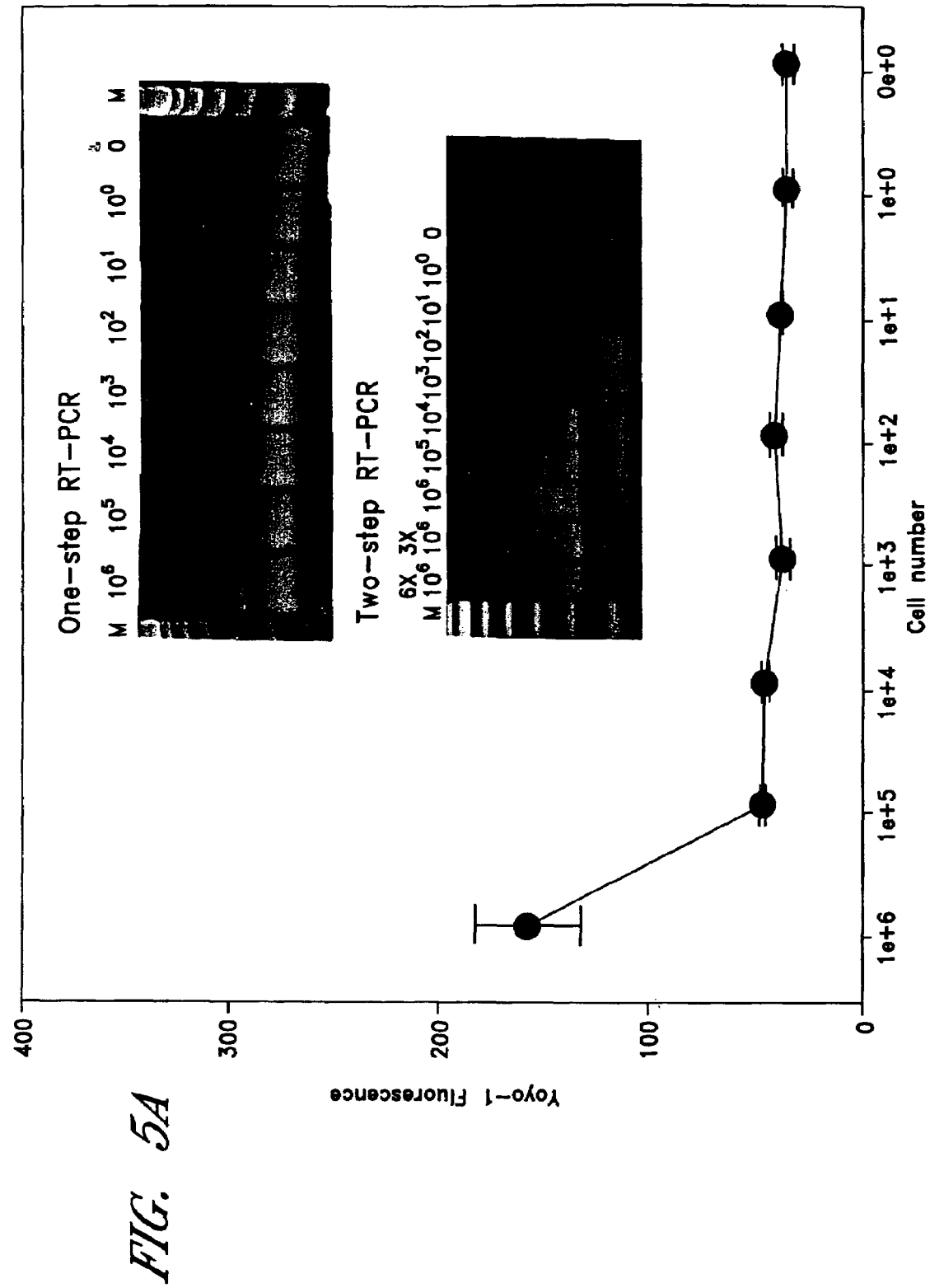
FIG. 5A is a graph showing hybridized mRNA measured by YOYO-1 at different dilutions of cell suspension. The upper inset shows the results of agarose gel electrophoresis showing hybridized mRNA measured by one-step RT-PCR using rTth polymerase. The lower inset shows the results of agarose gel electrophoresis showing hybridized mRNA measured by two-step RT-PCR using rTth polymerase.
Figure 5B:
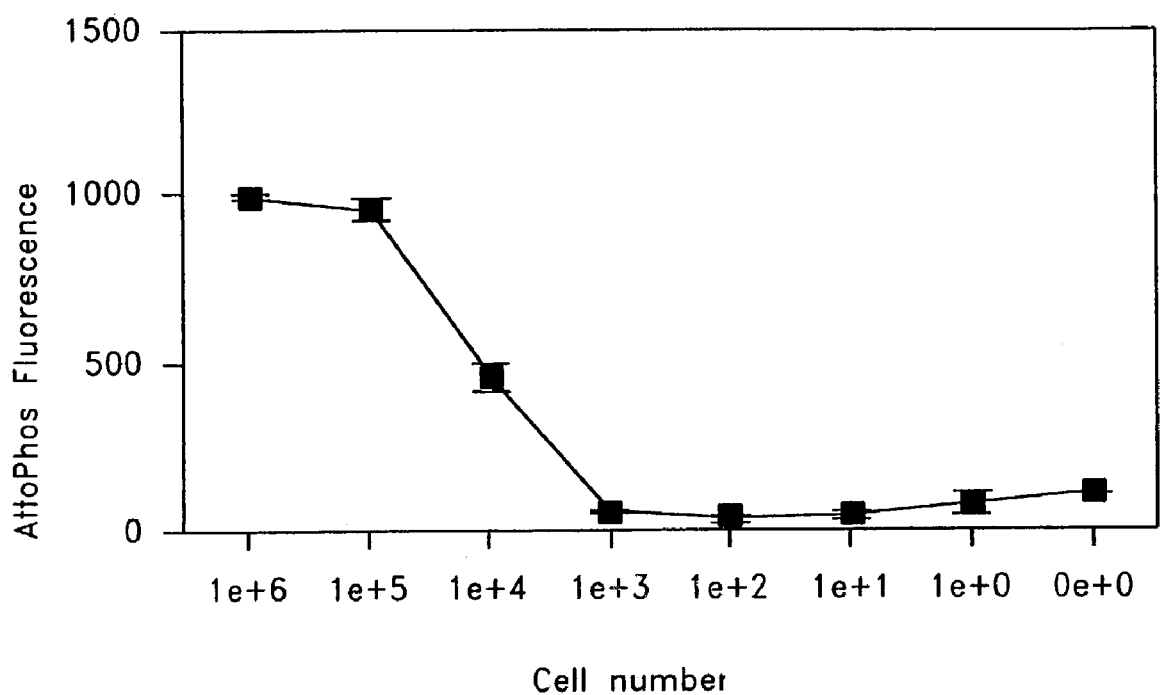
FIG. 5B is a graph showing hybridized mRNA measured by ATTOPHOS™ fluorescence at different dilutions of cell suspension.

Direct RT-PCR experiments were conducted at different dilutions of cell suspension. Various numbers of K562 cells were applied to the oligonucleotide-immobilized PCR microplates for hybridization. The resultant hybridized mRNA was used for either measurement of Yoyo-1, or one-step RT-PCR using rTth polymerase. That is, in FIGS. 5A and 5B, various amounts ($0-6\times10^6$) of K562 cells were suspended in lysis, and were applied to the oligonucleotide-immobilized PCR microplates for hybridization. In FIG. 5A, the amounts of hybridized mRNA were determined by YOYO™-1 fluorescence, as described above. In parallel experiments, captured mRNA was immediately subjected to one-step RT-PCR using rTth polymerase, as described above (Inset, upper). In FIG. 5B, in another series of experiments, cDNA was synthesized from captured mRNA using MMLV reverse transcriptase and immobilized oligo(dT) as a primer in the presence of biotin dUTP, followed by quantitation of cDNA synthesis, as described above. In parallel experiments, cDNA was synthesized on the oligonucleotide-immobilized PCR microplates by replacing biotin-dUTP with unlabeled dTTP, and PCR was conducted with rTth polymerase, as shown above (Inset, lower). The PCR products were separated by 2.0% agarose gel electrophoresis followed by staining with ethidium bromide. M indicates a 100 bp ladder. Each data point was the mean±S.D. from triplicate determinations.

As shown in FIG. 5B, significant ATTOPHOS™ signals were obtained even from as few as $10^4$ cells, suggesting 100-fold more sensitivity than YOYO™-1. More advantageously, when PCR was conducted from synthesized cDNA on the oligonucleotide-immobilized PCR microplates, PCR band was detected from as few as 10 cells (FIG. 5A, inset bottom).

In view of the foregoing, RT-PCR from synthesized cDNA on the oligonucleotide-immobilized PCR microplates (Two-step RT-PCR, FIG. 5A, lower inset) is approximately 100,000-fold more sensitive than conventional one-step RT-PCR, and bcr-abl transcript was detected from cell lysates containing only 10 cells (FIG. 5A, top inset). This is surprising because two-step RT-PCR required inefficient solid phase reverse transcription reaction, whereas one-step RT-PCR was conducted in more efficient liquid phase reaction by first dissociating mRNA from the oligonucleotide-immobilized PCR microplates. Since rTth was used for both experiments, the difference was not due to the enzyme. Because more primer dimers were formed in one-step PCR than two-step RT-PCR (FIG. 5A, top and lower insets: the clear band on each lane in the top inset indicate primer dimers), it is believed that primers are used for dimer formation during reverse transcription. In two-step RT-PCR, these primer dimers can be removed when the reaction mixture was switched from cDNA synthesis to PCR, whereas primer dimers formed during the initial reverse transcription phase exist throughout PCR.

Experiment 7: Intra- and Inter-Assay of Oligonucleotide Immobilization, Hybridization, and cDNA Synthesis In order to conduct quantitative analysis on the oligonucleotide-immobilized PCR microplates, well-to-well variation is a critical issue. One hundred pmol of oligonucleotides were applied to the oligonucleotide-immobilized PCR microplates for immobilization followed by YOYO™-1 fluorescence determination in a fluorescent plate reader, as described above (FIG. 6A●). One hundred ng of rabbit globin mRNA was applied to each well for hybridization, followed by YOYO™-1 fluorescence determination in a fluorescent plate reader, as described above (FIG. 6A■). One hundred ng of rabbit globin mRNA was applied to each well for hybridization, followed by cDNA synthesis in the presence of biotin-dUTP. ATTOPHOS™ fluorescence was then determined in a fluorescent plate reader, as described above (FIG. 6BΔ). Each data point was the mean±S.D. from 10 (Intra-assay) to 3 (Inter-assay) separate determinations.

Figure 6:
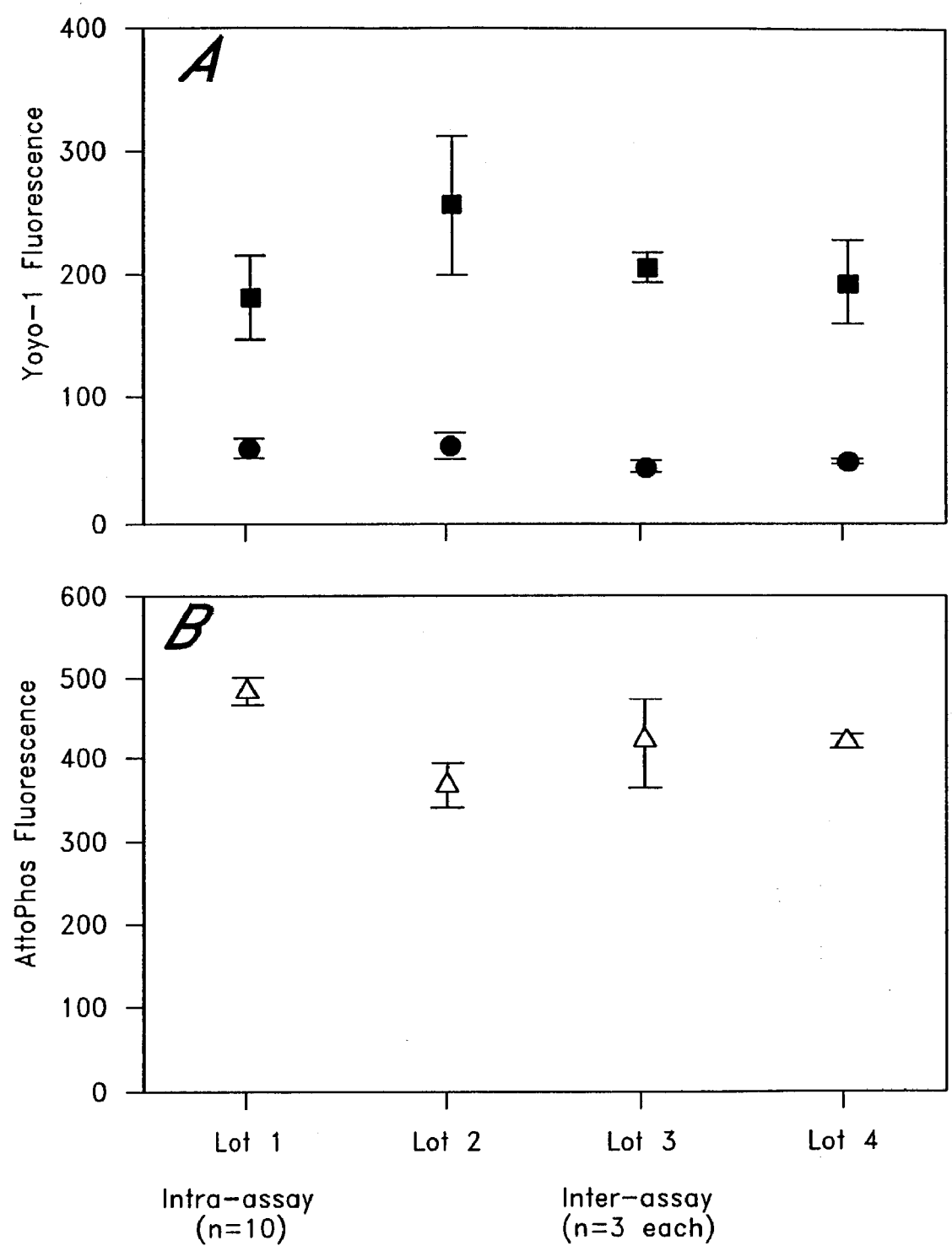
FIG. 6A is a graph showing well-to-well variation of the amounts of immobilized oligonucleotides and hybridized rabbit globin mRNA, measured by YOYO-1 fluorescence.
FIG. 6B is a graph showing well-to-well variation of the amounts of synthesized cDNA from captured rabbit globin mRNA measured by ATTOPHOS™ fluorescence.
Figure 7:
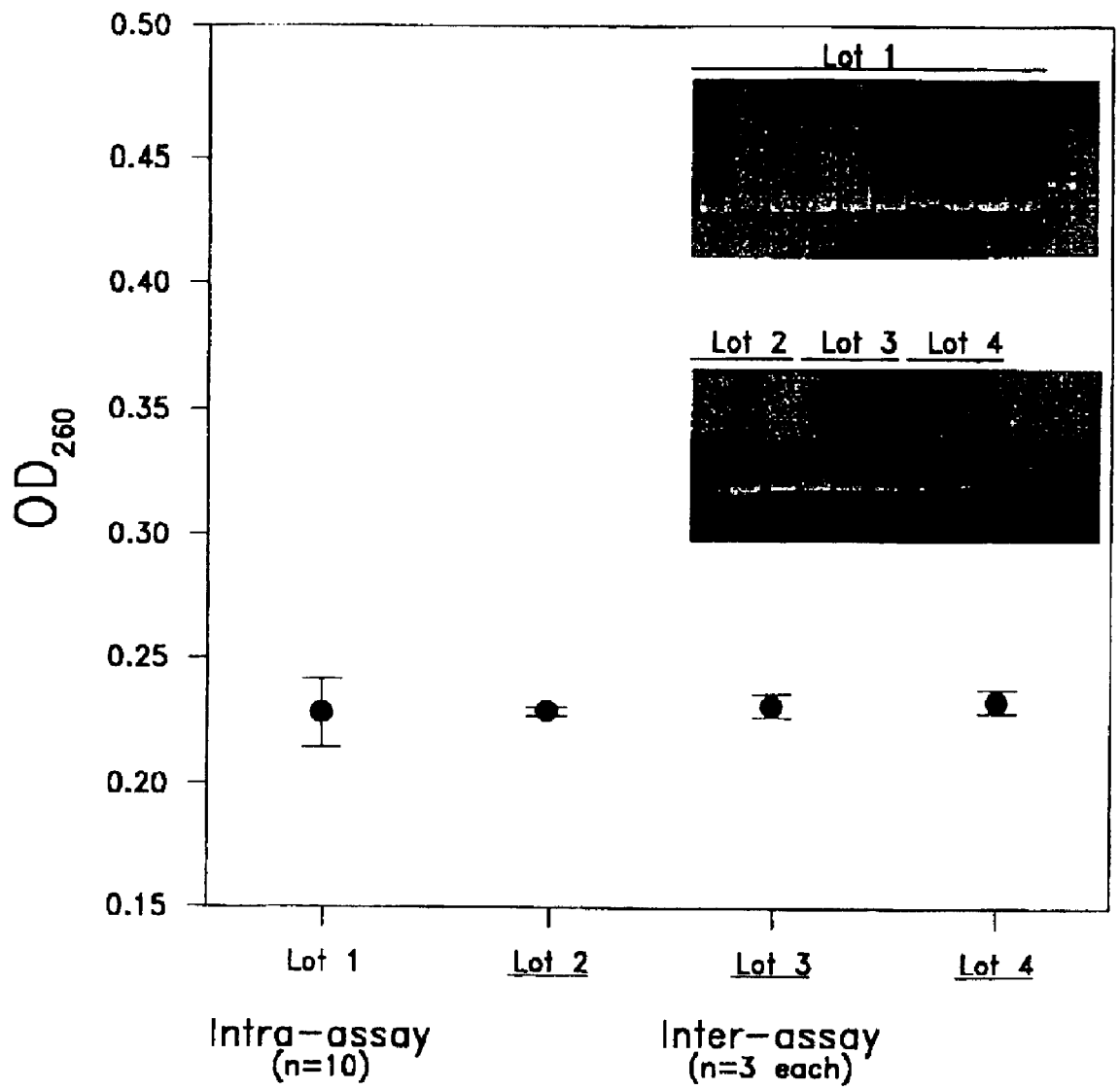
FIG. 7 is a graph showing well-to-well variation of the amounts of PCR products inter-assays and intra-assays (upper and lower insets).

As shown in FIGS. 6A and 6B, variation of the amounts of immobilized oligonucleotides (FIG. 6A●), hybridized rabbit globin mRNA (FIG. 6A■), and synthesized cDNA from captured rabbit globin mRNA (FIG. 6BΔ) were all less than 10-15% within a single microplate (Intra-assay) or multiple lots of microplates (Inter-assay). More importantly, the variation of the amount of PCR products in these intra- and inter-assays were also within 10% (FIG. 7). In FIG. 7, one hundred ng of rabbit globin mRNA was applied to each well for hybridization, followed by cDNA synthesis in the presence of unlabeled dTTP. PCR was then conducted with rabbit globin specific primers and Taq polymerase, as described in the Methods. The PCR products were separated by 2.0% agarose gel electrophoresis followed by staining with ethidium bromide. Right lanes indicate a 100 bp ladder. The amounts of PCR products were determined by measuring $OD_{260}$ (○). Each data point was the mean±S.D. from 10 (Intra-assay) to 3 (Inter-assay) separate determinations.

In view of the foregoing, less variation among wells and plates, excellent stability, and availability of various quality control protocols (e.g., FIGS. 6A, 6B, 7) make this technology very competitive.

Experiment 8: Stability of Oligonucleotide-Immobilized PCR Microplates

The oligonucleotide-immobilized PCR microplates were stored at room temperature (●), 55° C. (■) or 72° C. (Δ) for 2, 8 or 15 days. One hundred ng of rabbit globin mRNA was then applied to each well for hybridization, followed by cDNA synthesis in the presence of biotin-dUTP. ATTOPHOS™ fluorescence was then determined in a fluorescent plate reader, as described above. Each data point was the mean±S.D. from triplicate determinations.

Figure 8:
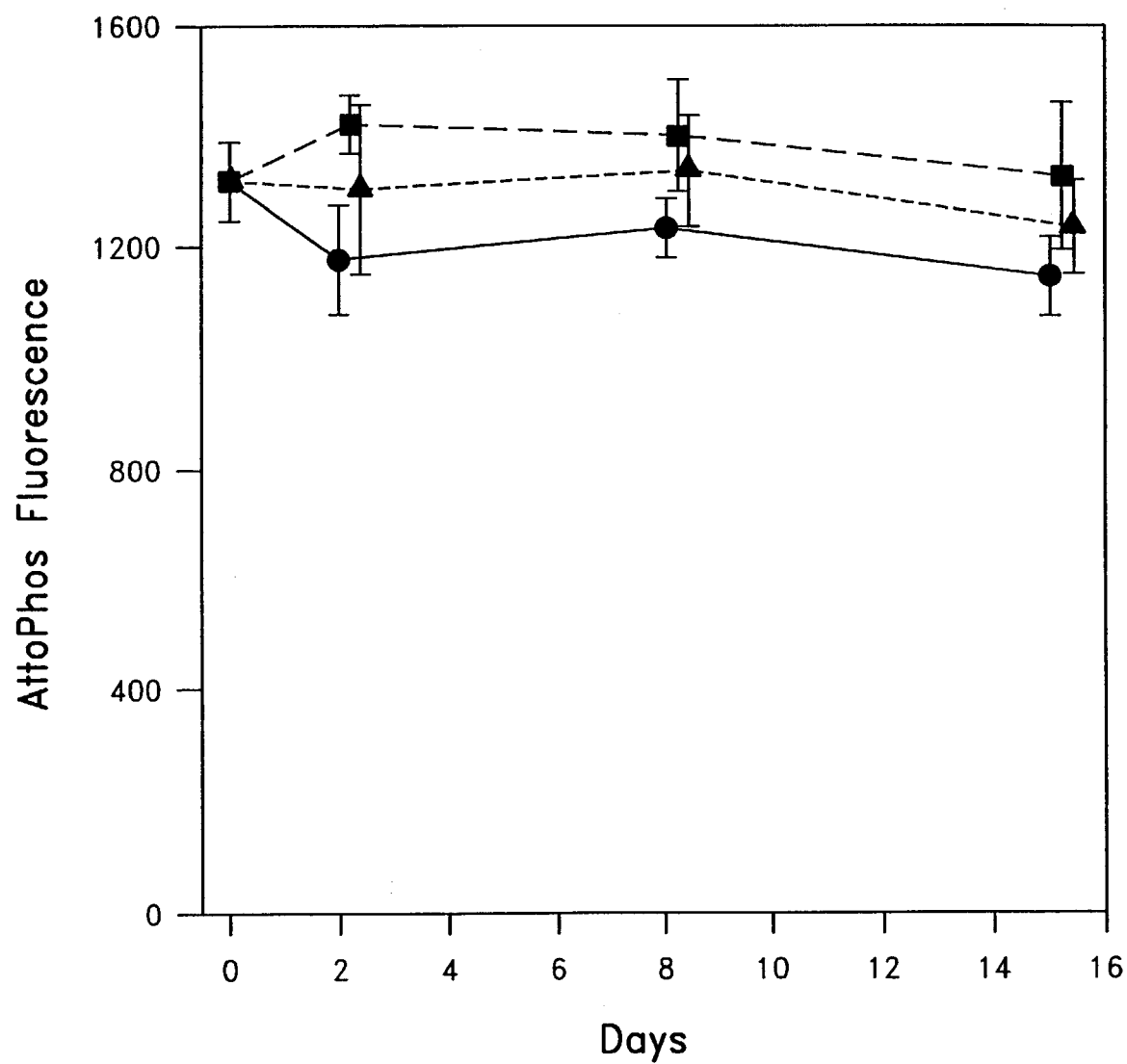
FIG. 8 is a graph showing storage stability of the PCR microplates, wherein the amounts of cDNA synthesis were determined by ATTOPHOS™ fluorescence.

As shown in FIG. 8, quantities of cDNA synthesis did not show any significant decreases even after storage at 72° C. for 15 days.

Experiment 9: Multiple PCRs from cDNA Synthesized on Oligonucleotide-Immobilized PCR Microplates K562 cells ($10^4$-$10^5$) were suspended in Lysis buffer and were applied to the oligonucleotide-immobilized PCR microplates for hybridization. The captured mRNA was converted to cDNA with MMLV reverse transcriptase as described above. As controls, some wells were treated identically but without MMLV reverse transcriptase. Then bcr-abl transcript was amplified by PCR with Taq polymerase, as described above (1st bcr-abl). After PCR, each well was washed with boiling DEPC water five times, and PCR was repeated with the same primer set (2nd bcr-abl). PCR was then repeated a third time with primer pair from G3PDH (3rd G3PDH). The PCR products were separated by 2.0% agarose gel electrophoresis, followed by staining with ethidium bromide. As a result, the, agarose gel electrophoresis indicates that PCR products of bcr-abl and G3PDH transcripts were not amplified from the wells of negative reverse transcription, indicating no "false" PCR products from contaminating genomic cDNA in the plates. More interestingly, the agarose gel electrophoresis confirms that bcr-abl and G3PDH transcripts were reamplified plural times from immobilized cDNAs from wells.

Experiment 10: Collection of Cytosolic mRNA Fraction to Oligonucleotide-Immobilized PCR Microplates from Various Cells by Glass Fiber Filter Various human cultured cell lines were used in this experiment: K562 leukemic, U937 leukemic, CaRI colon cancer, HepGII hepatoma, KatoIII stomach cancer, and CRL 5800 lung adenocarcinoma (American Type Culture Collection, Rockville, Md.). A 96-well filter plate with a single layer was made of glass fiber (Cambridge Technology grade 934AH, Brandel, Gaithersburg, Md.) in order to trap cells thereon. In preliminary experiments, the maximum capacity of cells trapped on the single layer of glass fiber filter membranes in each well of the 96-well filter plate was determined. Various numbers of cells ($10^2$ to $5 \times 10^6$) were applied to the filter plate assembled on top of a regular 96-well microplate, and centrifuged at 500×g for 10 min. The number of cells in the passed-through fraction collected in the well of the lower plates was measured with a hemocytometer. As a result, the maximum capacity of cells per well was approximately $2 \times 10^6$, $2 \times 10^6$, $10^6$, $5 \times 10^5$, $5 \times 10^5$ and $3 \times 10^5$ for K562, U937, CaRI, HepGII, KatoIII, and CRL 5800 cells, respectively, without any leakage of cells from glass fiber membranes.

In the next series of experiments, $10^5$ cells were applied to the filter plate, and cells were trapped onto the membrane by vacuum aspiration. The membranes were washed twice with PBS, and placed on top of the oligo(dT)-immobilized polypropylene/polyolefine microplate (GENEPLATE®-PP, AGCT) which would subsequently be used as a oligonucleotide-immobilized PCR microplate. Fifty µL of lysis buffer (10 mM Tris, pH 8.0, 1 mM EDTA, 0.5 M NaCl, 0.5% NP-40 detergent, and 20 mM vanadyl ribonucleoside complex (VRC, Gibco-BRL, Geithersburg, Md.)) was added to each well, and was immediately centrifuged at 500×g for 10 min to recover cytosolic RNA fraction into the oligonucleotide-immobilized PCR microplate. The lysis buffer allowed hybridization between oligo(dT) and poly(A) sequences of mRNA in the presence of RNase inhibitor VRC. After hybridization at room temperature for 1 hr, the oligonucleotide-immobilized PCR microplate was washed twice with a wash buffer (10 mM Tris, pH 8.0, 1 mM EDTA, and 0.5 M NaCl). At this stage, total mRNA was captured in each well of the oligonucleotide-immobilized PCR microplate for analysis. Because of the heat-stable characteristics of the oligonucleotide-immobilized PCR microplate, the oligonucleotide-immobilized PCR microplates were directly subjected to PCR without transfer of mRNA to PCR vessels.

Figure 9:
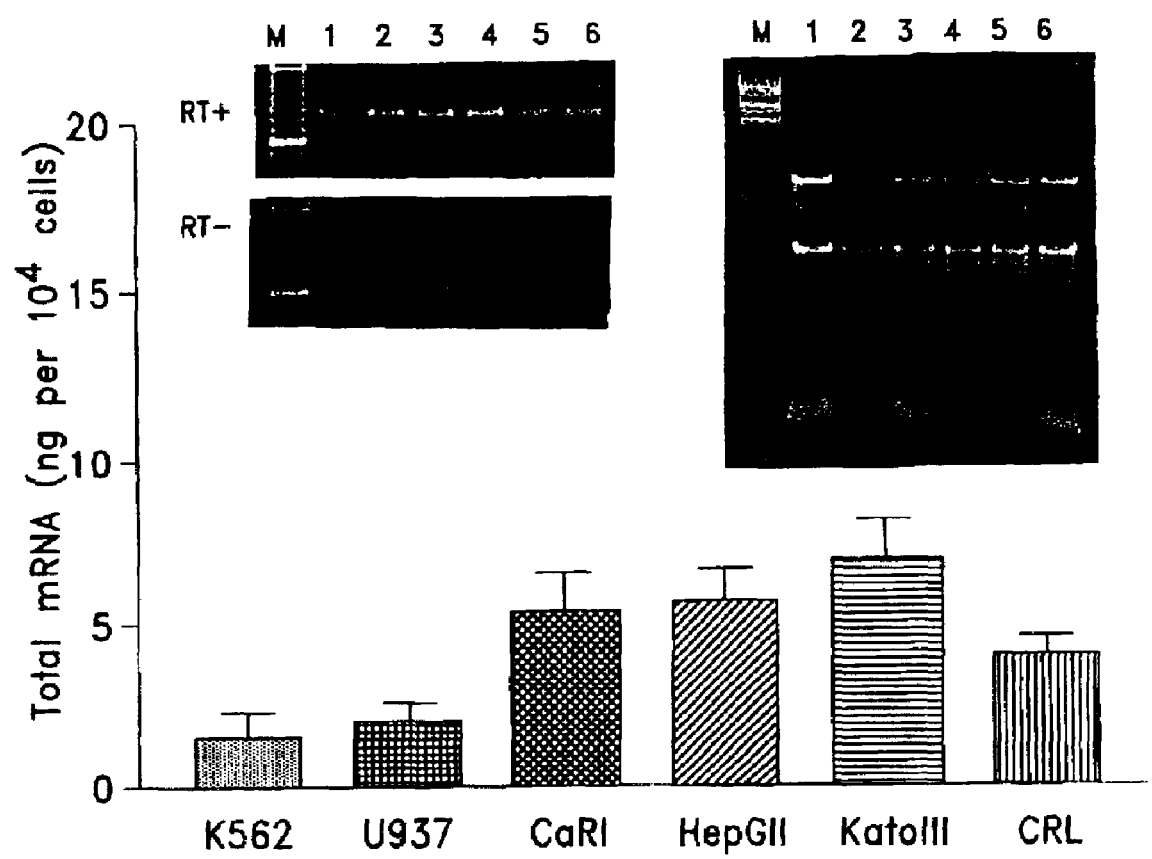
FIG. 9 is a graph showing measurement of mRNA and the results of agarose gel electrophoresis of PCR amplification of β-actin from various cultured cells which were subjected to lysis on a glass fiber filter to capture mRNA on oligo (dT)-immobilized polypropylene microplates.

Experiment 11: Measurement of mRNA and PCR Amplification of β-Actin from Various Cultured Cells Subsequent to Experiment 10, the first analysis was to amplify housekeeping genes from captured mRNA. The cDNA was synthesized by adding RT-buffer (50 mM Tris, pH 8.3, containing 75 mM KCl, 3 mM $MgCl_2$, and 10 mM DTT; 10 mM of each dNTP; and 100 U of MMLV reverse transcriptase (Gibco-BRL), and incubated at 37° C. for 1 hour. PCR was then conducted on the same plate, by replacing RT-buffer with PCR-buffer (10×PCR buffer, 1.5 mM $MgCl_2$, 100 µM of dNTPs, 1.5 units of Taq DNA polymerase (Perkin Elmer, Fostercity, Calif.), 0.5 µM each of upstream sense primer and downstream antisense primer of human β-actin (Clontech, Palo Alto, Calif.) in a final volume of 20 µL. PCR was conducted in a thermal cycler (MJ Research, PTC-100, Watertown, Mass.) with 35 cycles of 45 seconds at 94° C., 45 seconds at 60° C. and 2 minutes at 72° C. PCR products were analyzed in a 1.0% agarose gel electrophoresis with 0.5 µg/ml ethidium bromide. As shown in FIG. 9 (left insets: lane M, 100 bp DNA ladder; lane 1 K562; lane 2, U937; lane 3, CaRI; lane 4, HepGII; lane 5, KatoIII; lane 6, CRL5800), β-actin gene was successfully amplified from various cultured cells. Since intron sequences exist between sense and antisense primers, the size of β-actin PCR products were equal to that of intron-free mRNA. Furthermore, when starting PCR without cDNA synthesis, the β-actin gene was not amplified, suggesting that PCR was mRNA-specific, and not derived from contaminated DNA.

In parallel experiments, the amounts of captured mRNA on the oligonucleotide-immobilized PCR microplate were quantitated by the method published previously from our laboratory (Tominaga K, at al., "Colorimetric ELISA measurement of specific mRNA on immobilized-oligonucleotide-coated microtiter plates by reverse transcription with biotinylated mononucleotides", *Clin Chem* 1996:1750-1757, 1996) with minor modifications. In brief, the first strand cDNA was synthesized on the microplate by adding RT-buffer containing 250 µM biotin-dUTP instead of 10 mM of dTTP, and incubated at 37° C. for 1 hour. Each well was washed three times with wash buffer, and 50 µL of wash buffer containing 1:1000 dilution of streptavidin-alkaline phosphate conjugates (Clontech, Palo Alto, Calif.) were added to each well. Each well was incubated at room temperature for 30 min, and then washed three times with wash buffer. Finally 100 µL of AttoPhos (JBL Scientific, San Luis Obispo, Calif.) was added to each well and incubated at room temperature for 15 min. Fluorescence was determined in a CytoFluor 2300 (Millipore, Bedford, Mass.) at 430 nm excitation and 560 nm emission. In order to quantitate the amount of mRNA from fluorescence intensity, rabbit globin mRNA was used as a control as previously described (Tominaga K, et al., *Clin Chem* 1996:1750-1757, 1996). As shown in FIG. 9, captured mRNA from $10^4$ cells was approximately 5 ng from 5 different cell lines.

In order to further analyze the potential degradation of mRNA during hybridization, cytosolic fraction was collected after hybridization, and treated with two rounds of phenol/chloroform/isoamyl alcohol extraction followed by ethanol precipitation. RNA was then analyzed by agarose gel electrophoresis. As shown in FIG. 9 (right inset: Lane M, λ Hind III; lane 1, K562; lane 2, U937; lane 3, CaRI; lane 4, HepGII; lane 5, KatoIII; lane 6, CRL5800), 18s and 28s rRNA bands were clearly present in all cells even after 1 hour incubation at room temperature, suggesting that simple cytosolic fraction in the presence of VRC was essentially free from RNase activity.

In conclusion, complete RT-PCR from starting cell suspension can be conducted using just two plates; the glass fiber filter plate and the oligo(dT)-immobilized polypropylene/polyolefine plate. Furthermore, the 96-well format allows researchers to conduct RT-PCR in high throughput fashion with potential full automation. In this experiment, PCR products were analyzed by agarose gel electrophoresis, however, PCR products may be quantitated continuously by TaqMan system (Morris T, et al., *J Clin Microbiol* 34:p2933-6, 1996). This experiment proved that this system is a useful tool for high throughput RT-PCR.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A method of preparing cell lysate from target cells comprising nuclei, said lysate comprising cytosolic RNA, but substantially free of nuclear mRNA, said method comprising:

transferring the target cells to a filter plate provided with a membrane having a pore size such that the target cells are trapped, but cytosolic mRNA present in the cells can pass therethrough, wherein the target cells placed on the membrane form a cell layer; and passing a lysis buffer through the cell layer on the membrane to obtain the cell lysate of the target cells, wherein the lysis buffer comprises a mild detergent for destructing cell membranes but maintaining nuclei to be intact and a reagent for inhibiting RNase activity or inactivating RNase, said lysis buffer having a pH and salt concentration for hybridization.

2. A method according to claim 1, wherein the cell lysate is passed through the membrane of the filter plate by means of centrifugation, vacuum, or positive pressure.

* * * * *

SEQUENCE LISTING

<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: Primer cd4465 sense.

<400> SEQUENCE: 1
agtttcggag cggatgaatg c                                    21

<210> SEQ ID NO 2
<211> LENGTH: 22
<212> TYPE: DNA
<213> ORGANISM: Artificial Sequence
<220> FEATURE:
<223> OTHER INFORMATION: Primer cd4465 antisense.

<400> SEQUENCE: 2
ggggcatcag aattttggtt ga                                   22

<210> SEQ ID NO 3
<211> LENGTH: 20
<212> TYPE: DNA
<213> ORGANISM: Artificial Sequence
<220> FEATURE:
<223> OTHER INFORMATION: Primer for rabbit globin mRNA sense.

<400> SEQUENCE: 3
cgtggagagg atgttcttgg                                      20

```
<210> SEQ ID NO 4
<211> LENGTH: 22
<212> TYPE: DNA
<213> ORGANISM: Artificial Sequence
<220> FEATURE:
<223> OTHER INFORMATION: Primer for rabbit globin mRNA antisense.

<400> SEQUENCE: 4
aacgatattt ggaggtcagc ac                                        22

<210> SEQ ID NO 5
<211> LENGTH: 24
<212> TYPE: DNA
<213> ORGANISM: Artificial Sequence
<220> FEATURE:
<223> OTHER INFORMATION: Primer for bcr-able sense.

<400> SEQUENCE: 5
gaccaactcg tgtgtgaaac tcca                                      24

<210> SEQ ID NO 6
<211> LENGTH: 23
<212> TYPE: DNA
<213> ORGANISM: Artificial Sequence
<220> FEATURE:
<223> OTHER INFORMATION: Primer for bcr-able antisense.

<400> SEQUENCE: 6
aaagtcagat gctactggcc gct                                       23
```